US008805522B2

(12) United States Patent
Chapman-Jones

(10) Patent No.: US 8,805,522 B2
(45) Date of Patent: Aug. 12, 2014

(54) DRESSING FOR TISSUE TREATMENT

(75) Inventor: David John Chapman-Jones, Dover (GB)

(73) Assignee: Synapse Electroceutical Limited, Kent (GB)

( * ) Notice: Subject to any disclaimer, the term of this patent is extended or adjusted under 35 U.S.C. 154(b) by 109 days.

(21) Appl. No.: 10/574,252

(22) PCT Filed: Sep. 30, 2004

(86) PCT No.: PCT/GB2004/004165
§ 371 (c)(1),
(2), (4) Date: Nov. 28, 2006

(87) PCT Pub. No.: WO2005/032652
PCT Pub. Date: Apr. 14, 2005

(65) Prior Publication Data
US 2007/0239098 A1    Oct. 11, 2007

(30) Foreign Application Priority Data

Sep. 30, 2003    (GB) .................................... 0322851.7

(51) Int. Cl.
*A61N 1/00*    (2006.01)
(52) U.S. Cl.
USPC ................................................. 607/50; 607/2
(58) Field of Classification Search
USPC .......... 604/20, 23, 24, 289, 290, 293, 304, 65, 604/66, 19; 602/75; 607/2, 50, 144, 149
See application file for complete search history.

(56) References Cited

U.S. PATENT DOCUMENTS

| | | | |
|---|---|---|---|
| 4,141,359 A | | 2/1979 | Luntz et al. |
| 4,583,546 A | | 4/1986 | Garde |
| 4,895,154 A | | 1/1990 | Bartelt et al. |
| 4,982,742 A | * | 1/1991 | Claude ............................. 607/50 |
| 5,038,780 A | * | 8/1991 | Boetzkes ......................... 607/50 |
| 5,235,990 A | | 8/1993 | Dempsey |
| 5,395,398 A | | 3/1995 | Rogozinski |

(Continued)

FOREIGN PATENT DOCUMENTS

| | | |
|---|---|---|
| EP | 0 316 994 | 5/1989 |
| EP | 0 367 320 | 5/1990 |

(Continued)

OTHER PUBLICATIONS

PCT/GB2004/004165 International Search Report and Written Opinion of the International Searching Authority, dated Mar. 10, 2005.

(Continued)

*Primary Examiner* — Kevin C Sirmons
*Assistant Examiner* — Shefali Patel
(74) *Attorney, Agent, or Firm* — McKenna Long & Aldridge, LLP

(57) ABSTRACT

A dressing for treating a damaged tissue, incorporates a pair of electrodes and a conductive gel between the electrodes. An electric current passes between the electrodes through the gel to repair the damaged tissue. Sensors can be incorporated into the dressing along with a control unit. The control unit can vary the current supplied to the electrodes according to environmental parameters detected by the sensors. Alternatively, one or more pre-defined programs can be stored in the control unit for supplying an alternating current to the electrodes with a varying amplitude, frequency and waveform.

15 Claims, 5 Drawing Sheets

(56) References Cited

U.S. PATENT DOCUMENTS

| | | | |
|---|---|---|---|
| 5,397,338 A * | 3/1995 | Grey et al. | 607/115 |
| 5,578,022 A | 11/1996 | Scherson | |
| 5,792,090 A | 8/1998 | Ladin | |
| 5,855,570 A * | 1/1999 | Scherson et al. | 604/304 |
| 5,860,957 A * | 1/1999 | Jacobsen et al. | 604/156 |
| 5,891,182 A * | 4/1999 | Fleming | 607/50 |
| 5,944,685 A | 8/1999 | Muroki | |
| 5,974,344 A * | 10/1999 | Shoemaker, II | 607/149 |
| 6,117,109 A * | 9/2000 | Eggers et al. | 604/114 |
| 6,148,232 A * | 11/2000 | Avrahami | 604/20 |
| 6,162,460 A * | 12/2000 | Lee | 424/449 |
| 6,321,119 B1 | 11/2001 | Kronberg | |
| 6,411,853 B1 * | 6/2002 | Millot et al. | 607/50 |
| 6,567,696 B2 * | 5/2003 | Voznesensky et al. | 607/3 |
| 6,600,950 B1 * | 7/2003 | Tapper | 604/20 |
| 6,611,706 B2 * | 8/2003 | Avrahami et al. | 604/20 |
| 6,662,051 B1 | 12/2003 | Eraker et al. | |
| 7,167,752 B2 * | 1/2007 | Lin-Hendel | 607/46 |
| 7,486,989 B2 * | 2/2009 | Sun et al. | 604/20 |
| 2001/0044592 A1 * | 11/2001 | Li et al. | 604/20 |
| 2002/0010414 A1 * | 1/2002 | Coston et al. | 604/20 |
| 2002/0099412 A1 * | 7/2002 | Fischell et al. | 607/3 |
| 2002/0099425 A1 * | 7/2002 | Johnson et al. | 607/67 |
| 2002/0161323 A1 * | 10/2002 | Miller et al. | 604/20 |
| 2002/0173743 A1 * | 11/2002 | Tapper | 604/20 |
| 2003/0176825 A1 * | 9/2003 | Yavnai | 602/13 |
| 2004/0267189 A1 * | 12/2004 | Mavor et al. | 604/20 |

FOREIGN PATENT DOCUMENTS

| | | |
|---|---|---|
| GB | 2406519 A | 4/2005 |
| RU | 2090215 C1 | 9/1997 |
| SU | 1011128 | 4/1983 |
| WO | WO-94/22529 A1 | 10/1994 |
| WO | 9823326 A1 | 6/1998 |
| WO | 9840121 A1 | 9/1998 |
| WO | WO 99/20341 | 4/1999 |
| WO | 0002622 A1 | 1/2000 |
| WO | 0103768 A1 | 1/2001 |
| WO | WO 01/05445 | 1/2001 |
| WO | WO 01/13988 | 3/2001 |
| WO | WO 03/035166 | 5/2003 |

OTHER PUBLICATIONS

Search Report for GB 0322851.7 searched on claims 1-24 dated Jan. 28, 2004.

Search Report for GB 0322851.7 searched on claims 25-43 dated Mar. 29, 2006.

* cited by examiner

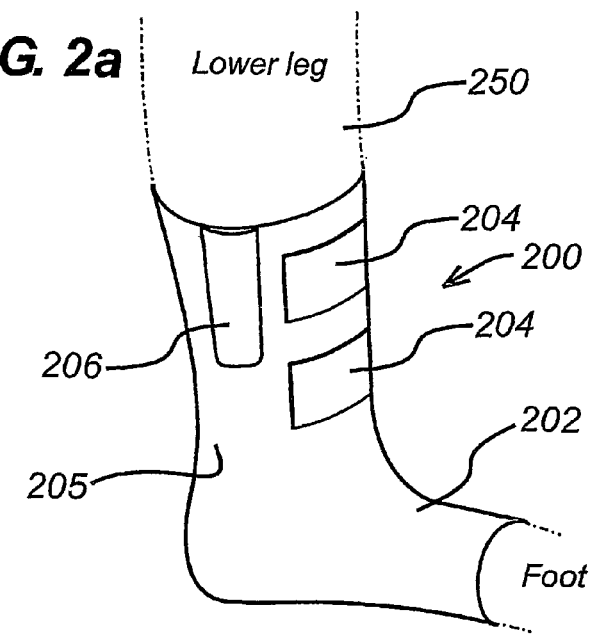
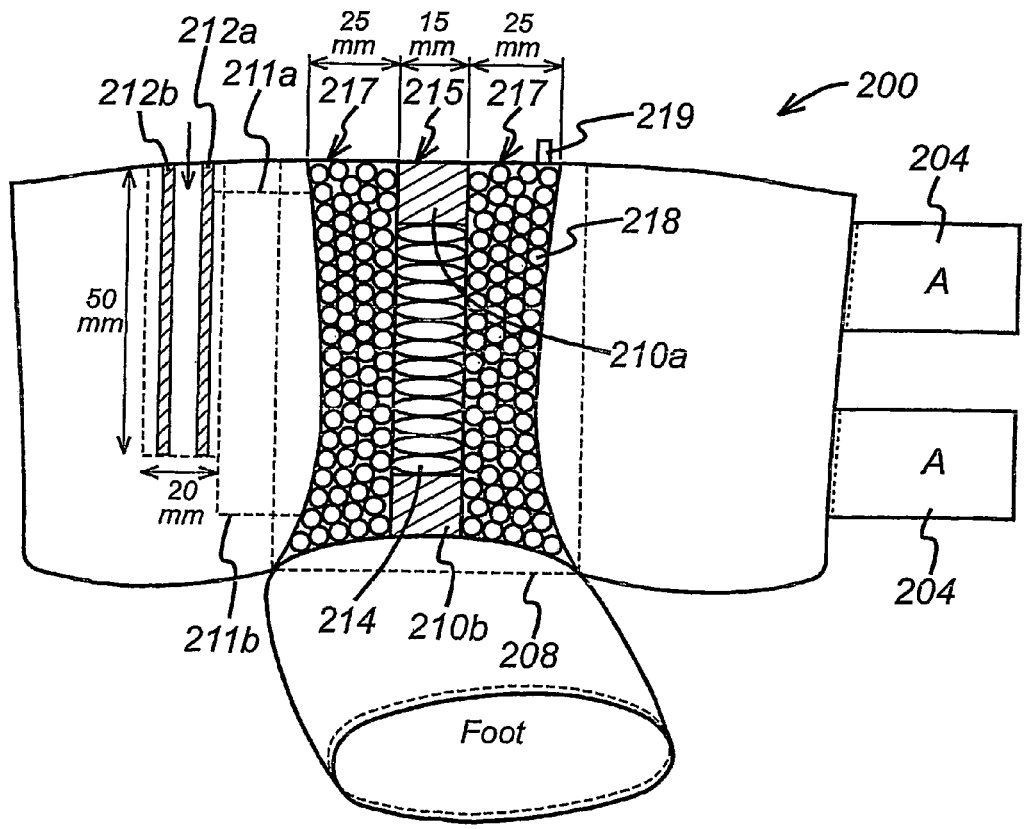

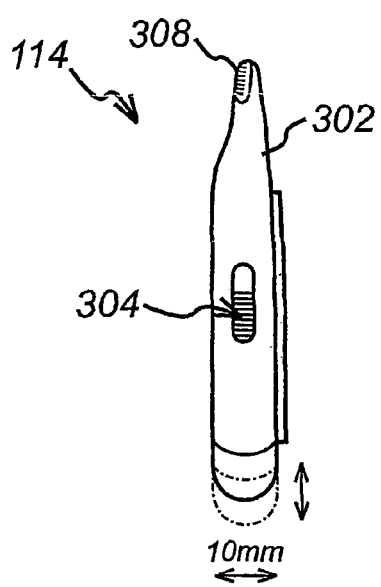
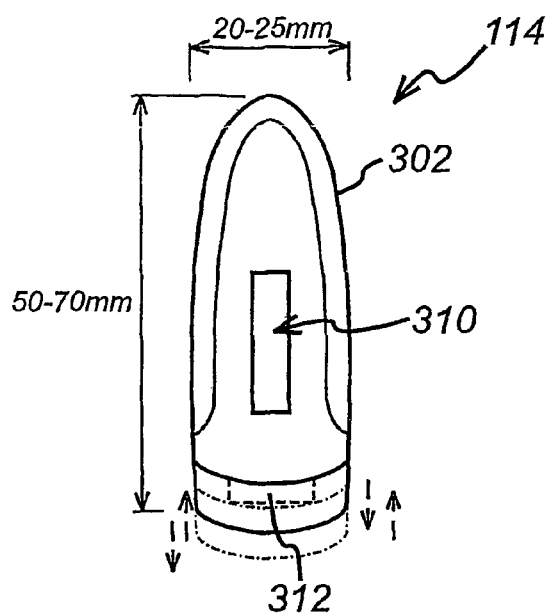
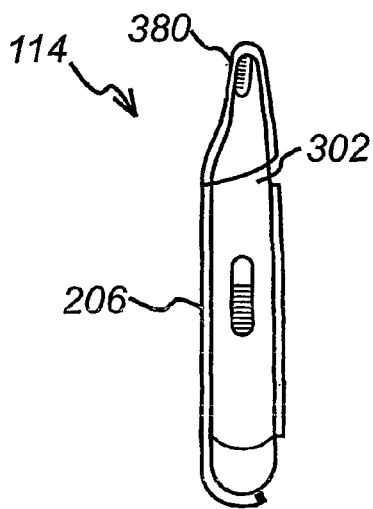
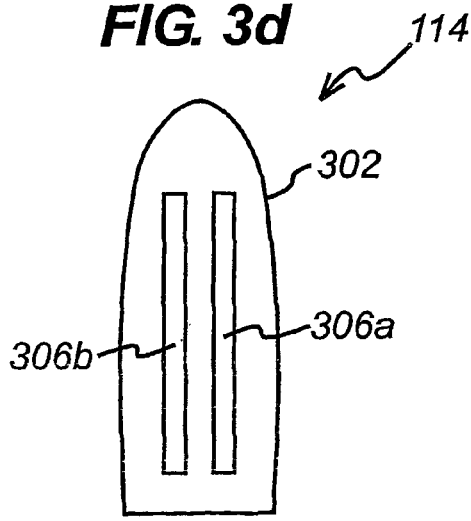
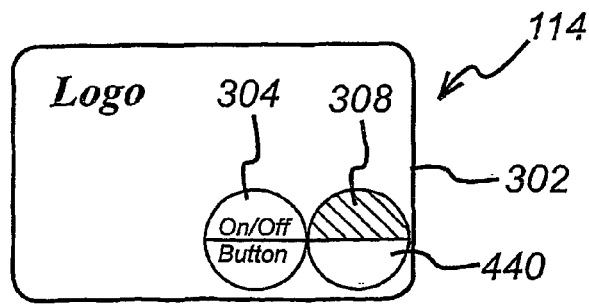

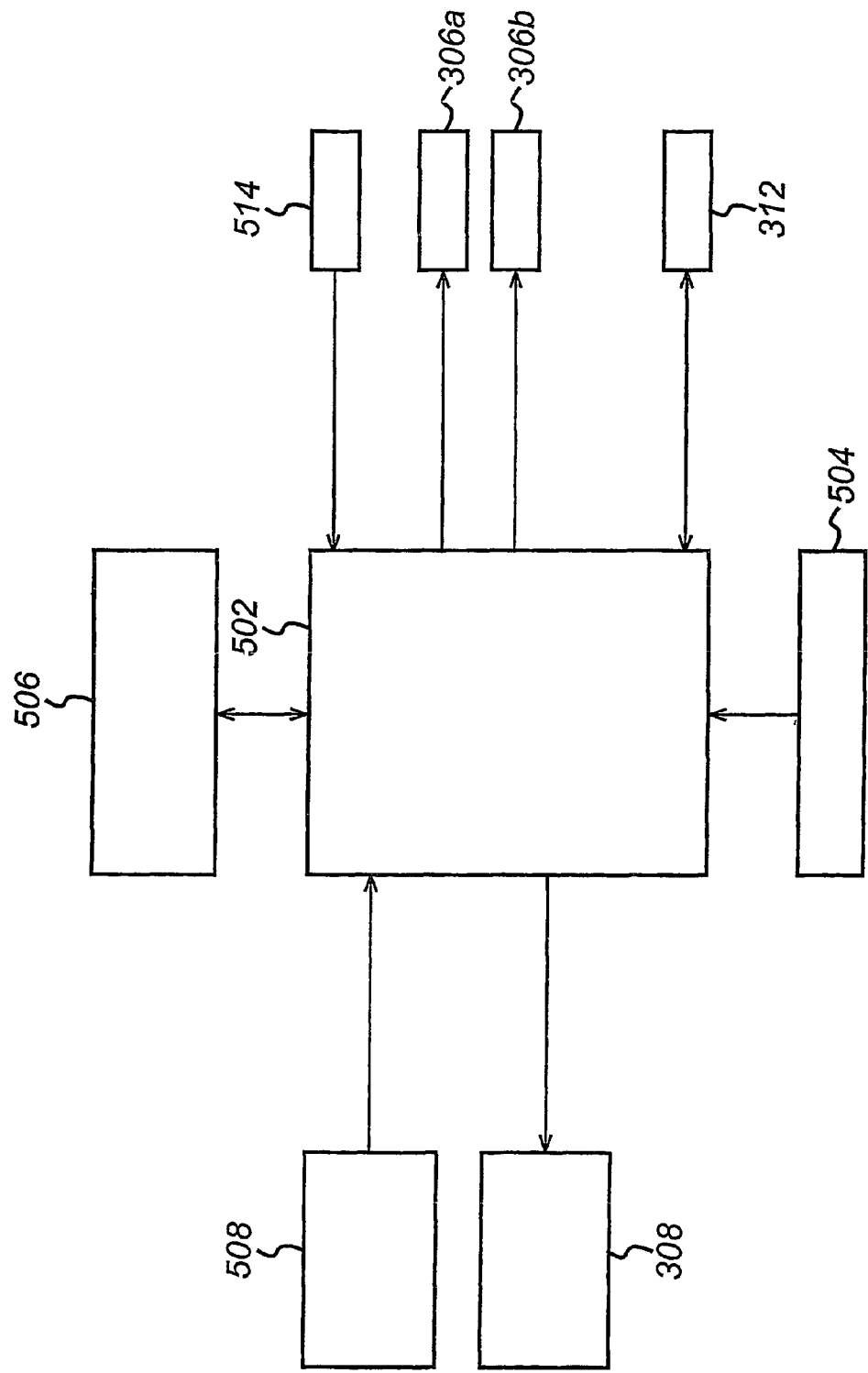

DRESSING FOR TISSUE TREATMENT

CROSS-REFERENCES TO RELATED APPLICATIONS

This application is the 35 U.S.C. 371 National State of International Application PCT/GB2004/004165, filed Sep. 30, 2004, which claimed priority to Great Britain application 0322851.7, filed Sep. 30, 2003.

FIELD OF THE INVENTION

The present invention relates to a dressing for treating tissue, in particular regeneration and repair of damaged tissue by application of electrical current to the tissue via electrodes contained in the dressing. For example, the damaged tissue may be skin and the damage may be a wound, such as a laceration or an incision. Alternatively, the damaged tissue may be tendons or ligaments and the damage caused by overuse or misuse. In addition, the present invention relates to a control unit and a gel for use with the dressing. Furthermore, the present invention relates to a method of providing a dressing for treatment of damaged tissue.

BACKGROUND OF THE INVENTION

Human or animal tissue is susceptible to many forms of damage. The damage can have many causes, including: non-complicated acute wounding, complicated chronic wounding, trauma, exercise related trauma and pathological damage.

An example of non-complicated acute wounding is a wound caused by surgery. Complicated chronic wounding may include wounds such as diabetic and venous ulcers, pressure sores and burns. Trauma wounds may include lacerations, contusions, incisions and blunt trauma such as bullet injuries. Exercise related trauma may occur to muscles, tendons and ligaments as a result of overuse, misuse and abuse. Pathological damage may cause joint problems, such as osteo-artritis and rheumatoid arthritis.

Repair of damaged tissue involves regeneration of tissue cells which occurs naturally as a result of repair mechanisms in the human or animal body. Often the natural repair of damaged tissue can be a lengthy process or does not occur at all as a result of the debilitating effects of infection or permanent damage to the tissue repair mechanisms.

The time taken to repair damaged tissue can cause many related problems, such as infection or re-infection of the damaged tissue, prolonged pain, temporary or permanent disability, scarring or aesthetic embarrassment for the injured person. For athletes and animals, such as horses, tissue damage prevents participation in training or competitions.

Thus, it is advantageous to provide a device for treating damaged tissue that promotes faster tissue repair.

Dressings for promoting tissue repair have been known for many years. These dressings are coated with substances which are absorbed into the damaged tissue and actively encourage cellular regeneration and prevent infection. However, such dressings only provide a slight improvement in the speed of the healing process. In the case of serious trauma or large areas of wounding, such dressings can become ineffectual and, in some cases, create more damage, for example by preventing oxygen getting to the surface of the wound. In the case of muscle, ligament or tendon damage, such dressings have no therapeutic effect at all, except to act as a support to the damaged area whilst repair occurs naturally.

In recent years, electrical treatment of damaged tissue has become known as an effective method of treatment of damaged tissue. This method involves supplying electrical current to a treatment area (i.e. either directly to the external wound or to the surface of the skin near the damaged tissue). Electrodes are fixed to the treatment area and a current generating device is connected to the electrodes. Originally, these devices supplied current at a fixed amplitude ranging from 1 to 10 milliamps. It was found that supplying current via electrodes to the treatment area significantly improved the time taken to repair damaged tissue. However, supplying current at such levels can result in discomfort for the user of the device. Therefore, more recent developments have included supplying electrical current to the surface of a treatment area with a constant amplitude waveform typically having an amplitude in the range of 10 to 800 microamps. Electrical current in this range is commonly known as "micro-current" and the electrical stimulation it causes cannot generally be detected by a user of the device.

Some existing current generating devices for supplying current to electrodes fixed to a treatment area are described in PCT Publication Nos. 00/02622, 01/03768, 98/23326 and 98/40121 and U.S. Pat. No. 5,395,398. All of the current generating devices described in the aforementioned documents comprise a remote unit with attached electrodes. The electrodes must be fixed to the treatment area, typically with tape. Wires connect the electrodes to the current generating unit which is remote from the treatment area. Treatment with such devices requires specialist knowledge about the operation of the device and electrodes, including knowing where to locate the electrodes and how to connect them to the current generating device. This often necessitates frequent visits to clinics by a user of the device. Furthermore, there is the annoyance of having to carry a separate current generating unit. Generally, the user has to remain immobile whilst treatment is being carried out.

PCT Publication No. 94/22529 describes an elastic housing with electrodes sewn into specific positions which can be worn by a user. When the housing is worn by a user, the electrodes are in the correct anatomic position for optimal treatment of the tissue which is to be treated. A current generating unit is fixed to the housing by insertion into a small pocket on the housing. The current generating unit is connected to the electrodes and supplies current to the electrodes with a waveform chosen from a number of different waveforms by the user using a control pad on the generating unit. The waveforms have constant amplitude and constant frequency.

One problem with the device of PCT Publication No. 94/22529 is that it is difficult to obtain good conductivity between the electrode and the treatment area. Since the electrodes are sewn into the housing, they are not necessarily fixed to the treatment area appropriately even when the housing is correctly worn. The size and shape of the treatment area around which the housing is worn can vary from one user to another and even change shape or size over time. Furthermore, the treatment area itself can change its physical condition as it is repaired. In particular, levels of infection, temperature and pH may vary over time. Thus, a treatment programme chosen for a particular patient when treatment is commenced may need to be varied as treatment progresses. In addition, it has become apparent that supplying alternating current with a simple waveform having constant amplitude and frequency is not necessarily the most effective waveform for encouraging cell regeneration.

Accordingly, it is an aim of the present invention to provide an improved device for treating damaged tissue that increases the rate of cell regeneration.

It is a further aim of the present invention to provide an improved device for treating damaged tissue that integrates separate elements into a single device that can easily be applied to a treatment area by an uninformed user and which has improved conductivity between the electrodes and the treatment area.

It is a still further aim of the present invention to provide an improved device for treating damaged tissue that integrates separate elements into a single device that can easily be applied to a treatment area by an uninformed user and which adapts its programme of treatment according to the physical condition of the treatment area.

SUMMARY OF THE INVENTION

The present invention is set out in the appendant claims.

In accordance with the aforementioned aims, there is provided, in a first aspect, a dressing for treating damaged tissue, the dressing incorporating:
   a pair of electrodes; and
   a conductive gel between the electrodes,
   such that, in use, an electric current passes between the electrodes through the gel to repair the damaged tissue.

In one embodiment of the present invention, the dressing further incorporates a holder for supporting a control unit, the holder comprising means for connecting the control unit to the electrodes.

In another embodiment of the present invention, the dressing further incorporates a control unit connected to the electrodes.

The dressing has the advantage of being easily fitted to the treatment area of a human or animal body, without requiring specialised assistance. The conductive gel provides good electrical connection between the electrodes and a treatment area.

Preferably, the dressing further comprises pockets in the surface adapted to hold the gel, such that the gel is forced out of the pockets onto a treatment area when the dressing is applied to the treatment area.

The gel is therefore contained in the dressing before use and is automatically applied to the treatment area when the dressing is strapped to the body.

Preferably, the gel is a conductive hydropolymer containing at least one type of a plurality of treatment molecules which are released when an electrical current from the electrodes passes through the gel.

The gel enters the wound or tissue surrounding the damaged tissue to provide good electrical conductivity between electrodes and damaged tissue. Activators in the gel enhance the regeneration of damaged tissue cells. The activators may be oxygen molecules.

In one embodiment of the present invention, the dressing further comprises:
   interlinked air pockets in the surface; and
   a valve linked to the air pockets,
   such that when the dressing is fixed to a treatment area, air supplied to the valve causes the pockets to expand and tighten the dressing against the treatment area.

Thus, improved connection between the damaged tissue and electrodes is obtained by forcing the dressing against the treatment area through expansion of the air pockets. In addition the dressing conforms with the shape of the body part to which it is applied, thereby making it comfortable to wear.

In a second aspect of the present invention, there is provided a dressing for treating damaged tissue, the dressing incorporating:
   a pair of electrodes;
   a sensor for detecting an environmental parameter on the damaged tissue,
   such that, in use, an electric current passes between the electrodes through the gel to repair the damaged tissue in accordance with the detected parameter.

Preferably, the sensor is adapted to produce a signal indicative of the environmental parameter.

Thus, no specialist assistance is required to fit a sensor to damaged tissue. Electrical current supplied to the electrodes can be controlled in accordance with differing environmental conditions which may vary from patient to another and change as the damaged tissue is repaired.

The environmental parameter may be one of an oxygen, pH, bacterial infection or temperature level.

Preferably, the connecting means comprises:
   a pair of contact electrodes in the holder; and
   a pair of wires embedded in the substrate, each wire connecting one of the contact electrodes to one of the pair of electrodes.

The electrodes may be carbon fibre electrodes and may be formed from a plurality of subsidiary electrodes connected to each other.

In a third aspect of the present invention, there is provided a control unit for use with the dressing, comprising:
   a housing;
   electronic circuitry in the housing;
   output electrodes connected to the electronic circuitry.

Preferably, the electronic circuitry comprises memory storing at least one programme for determining the amplitude, frequency and waveform of alternating current supplied to the output electrodes. The memory may be an EEPROM which can be updated with different programmes.

In one embodiment of the present invention, the control unit further comprises an i/o port connected to the electronic circuitry, such that an external device can connect to the control unit via the i/o port and update the memory and control operation of the control unit.

In another embodiment of the present invention, the control unit further comprises a wireless transceiver connected to the electronic circuitry, such that an external device can wirelessly connect to the control unit via the i/o port and update the memory and control operation of the control unit The wireless transceiver may communicate with an external device by infra-red or radio communication.

Advantageously, the control unit may comprise:
   a pair of activation electrodes; and
   a removable tab including a metallic strip connecting the activation electrodes,
   wherein the electronic circuitry detects when a current can pass between the activation electrodes and only supplies current to the output electrodes when the tab is removed such that no current passes between the activation electrodes. The tab is disposable. Thus, the control unit can be activated easily for single use.

In a fourth aspect of the present invention, there is provided a device for treating damaged tissue, comprising:
   a dressing for applying to a treatment area;
   a pair of electrodes affixed to a treatment surface of the dressing;
   a conductive gel applied to a section of the treatment surface; and a control unit connected to the electrodes and adapted to pass electrical current to the treatment area via the electrodes.

In a fifth aspect of the present invention, there is provided a device for treating damaged tissue, comprising:
 a dressing for applying to a treatment area;
 a pair of electrodes affixed to a treatment surface of the dressing;
 a sensor attached to the dressing for detecting an environmental parameter at the treatment area; and
 a control unit connected to the electrodes and the sensor and adapted to pass electrical current to the treatment area via the electrodes according to the detected parameter.

Preferably, the control unit is attached to the dressing and the sensor is integral with the control unit.

In a sixth aspect of the present invention, there is provided a device for treating damaged tissue, comprising:
 a dressing for applying to a treatment area,
 a pair of electrodes affixed to a treatment surface of the dressing;
 a control unit connected to the electrodes and adapted to pass alternating current to the treatment area via the electrodes,
 wherein the control unit constantly varies the amplitude and/or the frequency of the alternating current.

It has been found that constantly varying the amplitude and/or the frequency of the alternating current provides enhanced tissue regeneration over previously known methods of electrical tissue stimulation.

Preferably, the alternating current is varied between 50 and 500 microamps. Additionally, the frequency of the alternating current may be varied between 10 and 900 hertz. Furthermore, the time period between each variation of amplitude and/or frequency may be 0.1 s. These parameters provide the fastest rate of tissue regeneration without the electrical stimulation being discernible by a user of the device.

Preferably, the alternating current has a ramp waveform.

In one embodiment of the present invention, the control unit is etched into the substrate. Thus, an integrated device including a control unit can be easily manufactured.

In an alternative embodiment of the present invention, the control unit comprises:
 a housing;
 electronic circuitry in the housing;
 output electrodes connected to the electronic circuitry; and
 a power supply in the housing connected to the electronic circuitry.

In a seventh aspect of the present invention, there is provided, a gel for use in treating damaged tissue, comprising:
 a conductive hydropolymer; and
 a plurality of treatment molecules configured to be released from the gel when an electrical current passes through the gel.

BRIEF DESCRIPTION OF DRAWINGS

Specific embodiments of the invention are now described with reference to the following drawings, in which:

FIG. 1b is a plan view of the device of FIG. 1a;

FIG. 2a is a perspective view of a dressing for treatment of damaged tissue according to a second embodiment of the present invention;

FIG. 2b is a front view of the dressing of FIG. 2a prior to application;

FIG. 3a is a side plan view of one embodiment of a control unit for use with the dressings of FIGS. 1a, 1b, 2a and 2b;

FIG. 3b is a front plan view of the control unit of FIG. 3a;

FIG. 3c is a side plan view of the control unit of FIG. 3a;

FIG. 3d is a rear plan view of the control unit of FIG. 3a;

FIG. 4 is a plan view of an alternative embodiment of a control unit for use with the dressings of FIGS. 1a, 1b, 2a and 2b;

FIG. 5 is a representation of the components of the control unit of FIGS. 3a, 3b, 3c, 3d and 4.

DETAILED DESCRIPTION OF DRAWINGS

The present invention will be described below relative to a specific embodiment. Those skilled in the art will appreciate that the present invention may be implemented in a number of different applications and embodiments and is not specifically limited in its application to the particular embodiment depicted herein. In particular, the present invention will be discussed below in connection with treating humans, although those of ordinary skill will recognise that the device could be modified to be used to treat animals.

Figure 1A:
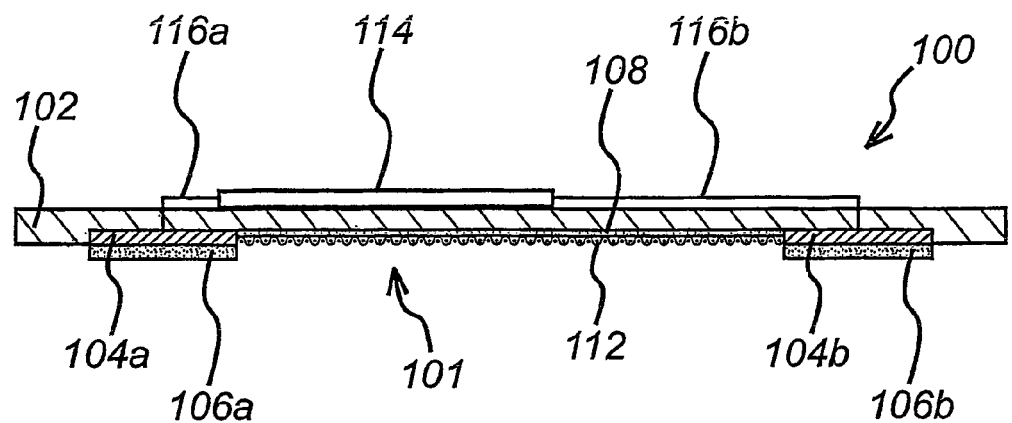
FIG. 1a is a planar cross-section view of a device for treatment of tissue according to a first embodiment of the present invention.

FIG. 1a is a planar cross-section view of a device (100) for treatment of damaged tissue according to a first embodiment of the present invention. The device (100) can be used in place of a conventional dressing and applied to an external tissue wound and fixed to the tissue using, for example, adhesive or conventional strapping.

The device (102) comprises a conventional dressing (102) which supports a pair of carbon-fibre electrodes (104a, 104b) on a treatment surface (101). There is a conducting electrode gel (106a, 106b) on treatment surfaces of the electrodes (104a, 104b). The electrode gel (106a, 106b) melts at 35° C. (i.e. when it is applied to the surface of human tissue) thereby releasing conducting gel onto the surface of a treatment area to which the dressing (102) is applied between the electrodes (104a, 104b) and the tissue. The conducting electrode gel (106a, 106b) ensures good electrical contact with the tissue.

The dressing (102) also comprises an tissue gel (108) and mesh material (112) fixed over the tissue gel (108). The mesh material (112) allows exudate from a wound to which the dressing is applied to be absorbed into the dressing (102) whilst allowing the tissue gel (108) to flow through it so that it can be absorbed by a wound being treated.

On an opposing side to the treatment surface (101), a control unit (114) is fixed to the dressing (102). The control unit (114) is connected to the electrodes (104a, 104b) via wires (116a, 116b). In operation, electrical current flows from a first electrode (104a) through the electrode gel (106a) via tissue and electrode gel (106b) to the second electrode (104b). The control unit (114) will be described in more detail below with reference to FIGS. 3a, 3b, 3c and 4 to 6. However, it should be appreciated that when the control unit is permanently fixed to the dressing (102) as shown in FIG. 1a, this can be achieved by etching the control unit (114) directly on to the dressing (102). As a result, the size of the device (100) can vary from very small "microcapsules" equivalent to the size of a grain of rice up to a size which is capable of covering large areas of human or animal tissue.

The tissue gel (108) is hydropolymer conducting gel with chemical activators that release oxygen molecules when an electric current flows through the tissue gel (108). The tissue gel (168) is absorbed by the wound being treated so that an electrical current can pass more easily through the wound. The oxygen molecules are absorbed by the tissue being treated and enhance the cell regeneration process, thereby decreasing the time taken for the wound to heal.

The gel (108) is formed of two different types of constituent substances, with each type being held in a separate layer of matrix material. There are three layers of matrix material arranged alongside each other in a sandwich configuration A common component of all layers is hydrocolloid particles with 70% water saturation. In addition, the middle layer contains 1000 mg/sq cm ascorbic acid and silver particles at 500 mg/sq cm. The middle layer is also saturated with 100% oxygen. The entire gel (108) including the matrix material is pH neutral.

The whole device (100) is designed to be disposable once it has been used. This may be when treatment has finished, when the dressing (102) needs to be replaced so that the wound can be examined or cleaned or when a battery in the control unit (114) has expired.

Figure 1B:
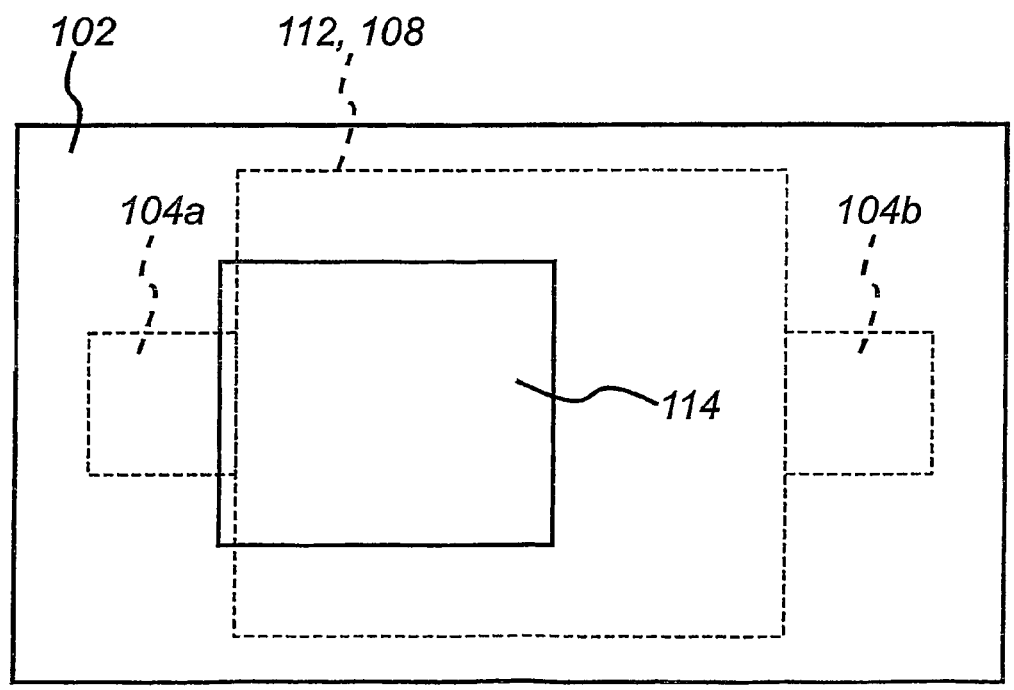

FIG. 1b is a plan view of the device of FIG. 1a.

FIG. 2a is a perspective view of a dressing (200) for treatment of damaged tissue according to a second embodiment of the present invention. The dressing (200) is in the form of an elastic cuff which can be used in place of a conventional elastic support. The dressing (200) can be applied to either an external tissue wound or to a treatment area where there is internal damage to tendons, muscles or ligaments.

The dressing (200) comprises a substrate (202) which is held in place over a treatment area on a limb (250) of a body by velcro straps (204) attached to an external surface (205) of the substrate (202). There is a holder (206) in the form of a pocket formed in the external surface of the substrate (202) for receiving a control unit (114). The substrate (202) is formed from an elastic blend which comprises 78% neoprene rubber, 20% stretch nylon and 2% memoflex weave. The substrate (202) is formed to fit tightly and comfortably around a particular part of the body. The body part shown in FIG. 2a is the ankle of a human.

FIG. 2b is a cross-section view of the dressing (200) of FIG. 2a and shows the internal components of the dressing (200) on a treatment side of the substrate (202). There are carbon fibre tissue electrodes (210a, 210b) embedded in a treatment surface (208) of the substrate (202). The tissue electrodes (210a, 210b) are connected via wires (211a, 211b) to input electrodes (212a, 212b) in the holder (206). The input electrodes (212a, 212b) extend the entire length of the holder (206) across one side of the pocket and are adapted to connect with corresponding output electrodes on an external surface of a control unit (114) (see below).

Between the tissue electrodes (210a, 210b) and embedded in the treatment surface (208) of the substrate (202) is a first region (215) of gel pockets (214). The pockets (214) are formed of cotton woven into the treatment surface (208) of the substrate (202). The pockets contain tissue gel (108) as described above with reference to FIGS. 1a and 1b. The tissue gel (108) is forced out of the pockets (214) when the dressing (200) is strapped tightly to the body. If the treatment area includes an external wound, then the tissue gel (108) is absorbed into the area of the wound as described above with reference to FIGS. 1a and 1b. If tissue damage is internal, then the tissue gel (108) may be adapted to be absorbed through the skin into the damaged tissue to improve electrical conduction through the internally damaged tissue.

The width of the first region (215) of gel pockets (214) is substantially the same as the width of the tissue electrodes (210a, 210b) and in the embodiment shown in FIG. 2b, this width is approximately 15 mm. Thus, the entire first region (215) between the tissue electrodes (210a, 210b) is a first region (215) of gel pockets (214). The damaged tissue should therefore be located between the tissue electrodes (210a, 210b) so that electrical conductivity through the damaged tissue is enhanced.

Extending along each side of the tissue electrodes (210a, 210b) and first region (215) of gel pockets (214) is a second region (217) of interlinked air pockets (218). The width of the second region is approximately 25 mm. The air pockets (218) are interlinked so that air inserted through a valve (219) at an edge of the substrate (202) causes all of the air pockets (218) to expand thereby forcing the tissue electrodes (210a, 210b) and the gel pockets (214) against the treatment area of the body around which the dressing (200) is fixed.

With reference to FIGS. 3a, 3b, 3c and 3d, one embodiment of a control unit (114) for use with the dressings of FIGS. 1a, 1b, 2a and 2b is shown. In the embodiment shown in FIGS. 1a and 1b, the control unit is permanently fixed to the dressing (100), whereas in FIGS. 2a and 2b, the control unit (114) is designed to be removable from the holder (206). However, the control unit (114) can either be integrated permanently with the device (100) of FIGS. 1a and 1b or removably integrated with the dressing (200) of FIGS. 2a and 2b. In either of these two embodiments, the control unit (114) functions in exactly the same way for both the device (100) and the dressing (200).

The control unit (112) comprises a housing (302) on which a bipolar power switch (304) is mounted. The housing contains electronic circuitry (not shown) and a power source (not shown). Output electrodes (306a, 306b) connected to the electronic circuitry are mounted on the housing (302). For the embodiment shown in FIGS. 2a and 2b, the position of the output electrodes (306a, 306b) corresponds with the position of the input electrodes (212a, 212b) mounted in the holder (206) of the dressing (200). For the device (100) of FIGS. 1a and 1b, the wires (116a, 116b) will be hard-wired directly into the electronic circuitry.

One or more of the led indicators (308) is mounted on an upper portion of the housing (302) so that when the control unit (114) is inserted into the holder (206) of FIGS. 2a and 2b, one or more of the led indicators (308) protrudes from the top of the holder (308) so that they can be seen by a user of the dressing (200). A front surface of the control unit (114) has a tab (310) which is temporarily fixed over two activation electrodes (not shown). The tab (310) includes a metallic strip which connects the two activation electrodes when it is fixed in place.

When the switch (304) is in an 'on' position, the led indicator (308) glows continuously and the power supply powers the electronic circuitry, passing an electric current through the metallic strip. However, electrical current is not output through the output electrodes (306a, 306b) until the control unit (114) is activated by removing the tab (310) and the electronic circuitry detects that no current is now passing between the two activation electrodes.

Additionally, there is an opening in the housing (302) to an i/o port (312). The i/o port (312) is connected to the electronic circuitry and allows an external device, such as a personal computer, to reprogram an EEPROM in control unit (114). The EEPROM contains programmes for supplying current in a variety of different waveforms to the tissue via the output electrodes (306a, 306b).

A sensor port (not shown) is mounted on the housing (302). A variety of different sensors may be connected to the sensor port. The electronic circuitry can measure the output of a sensor connected to the sensor port and adjust the waveform of the electrical current which is output from the output electrodes (306a, 306b) depending on the value of the parameter being measured by the sensor. Different types of sensor can be connected to the sensor port, each type of sensor measuring one or more different parameters, for example one or more of oxygen, pH, bacterial infection or temperature levels.

The control unit (114) in FIG. 3c is shown in the holder (206) of FIGS. 2a and 2b. There is a transparent flap (380) affixed to the top of the holder which functions to hold the control unit (114) in place in the holder (206) and allow one or more of the led indicators (308) to be viewed externally from the holder (206) by the user.

FIG. 4 is a plan view of an alternative embodiment of a control unit for use with the dressings of FIGS. 1a, 1b, 2a and 2b. The housing (302) of the control unit (114) is made of plastic and is of the size and shape of a conventional credit card (i.e. approximately 5 mm deep, 85 mm long and 52 mm wide). This way, the control unit (114) is portable and can, for example, be carried by a user in their purse or wallet On the front of the control unit (114) is a power switch (304) and one or more led indicators (308) which have already been described above. There may also be a separate battery indicator (440) for showing when the battery level is low. The control unit (114) of FIG. 4 is designed to be disposable after a programme of treatment has been completed.

FIG. 5 is a representation of components (500) of the control unit of FIGS. 3a, 3b, 3c and 4. A microcontroller (502) is powered by battery (504). The microcontroller generates current of varying amplitude and frequency and supplies it to electrodes (306a, 306b) depending on the programme which is selected by switches (508). A plurality of switches (508) which includes switch (304) allows interaction with the microcontroller (502) to determine whether the device is switched on and which programme of current is being supplied to the electrodes (306a, 306b). The programmes are stored in EEPROM (506) which is bi-directionally connected to microcontroller (502). The programmes can be changed (i.e. removed, updated and edited) through interaction with an external device via i/o port (312). A sensor port (514) allows one or more different sensors to be connected to the microcontroller (502) to provide feedback of external environmental parameters to determine the output form of current to the electrodes (306a, 306b). The output form of current will vary depending on the programme selected and the value of the detected parameter.

Figure 6:
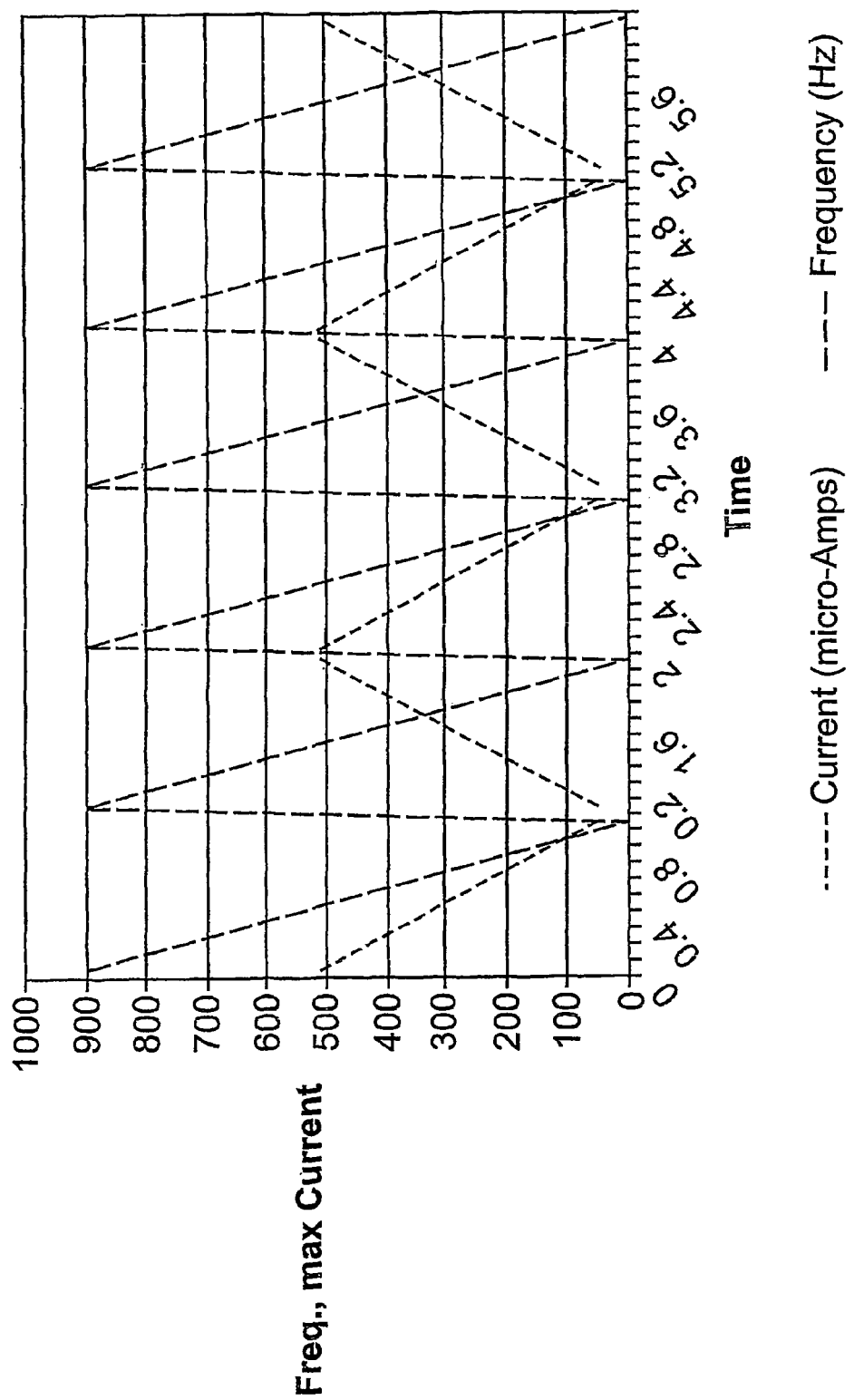
FIG. 6 is representation of the variation in amplitude and frequency output by the control units of FIGS. 3a, 3b, 3c and 5.

FIG. 6 is a representation of the alternating current waveform output by the control units of FIGS. 3a, 3b, 3c, 3d and 4. In experiments carried out by the applicant, it has been determined that the scanning programme shown in table 1 below (i.e. a programme in which the amplitude and/or frequency of the alternating current being supplied to damaged tissue is varied) is the most effective at encouraging tissue cell regeneration and hence repair of damaged tissue. The programme is programmed into the EEPROM (506) within the control unit (114). As mentioned above, additional programmes can also be programmed into the EEPROM (506) and selected using a multi-way switch (not shown) or other switches (508) on the control unit (114).

TABLE 1

Variation of amplitude and frequency of current in a scanning programme

| Step | Amplitude I/ μA | Frequency/ Hertz |
|---|---|---|
| 1 | 500 | 900 |
| 2 | 450 | 800 |
| 3 | 400 | 700 |
| 4 | 350 | 600 |
| 5 | 300 | 500 |
| 6 | 250 | 400 |
| 7 | 200 | 300 |
| 8 | 150 | 200 |
| 9 | 100 | 100 |
| 10 | 50 | 10 |
| 11 | 50 | 900 |
| 12 | 100 | 800 |

TABLE 1-continued

Variation of amplitude and frequency of current in a scanning programme

| Step | Amplitude I/ μA | Frequency/ Hertz |
|---|---|---|
| 13 | 150 | 700 |
| 14 | 200 | 600 |
| 15 | 250 | 500 |
| 16 | 300 | 400 |
| 17 | 350 | 300 |
| 18 | 400 | 200 |
| 19 | 450 | 100 |
| 20 | 500 | 10 |

The waveform of the alternating current is a ramp waveform and the time period for each step is 0.1 s. Optimal regeneration occurs with the programme running for 30 minutes.

An alternative programme which can also be programmed into the control unit (114) is one of using a constant amplitude and frequency alternating current with a rectified waveform using positive polarity. With an amplitude of 40 μA and a frequency of 10 Hertz, it has been shown that this alternative programme provides optimal electro-stimulation for fibroblast regeneration and collagen production.

It will of course be understood that the present invention has been described above purely by way of example, and that modifications of detail can be made within the scope of the invention.

The invention claimed is:

1. A device for treating a damaged tissue, the device comprising:
    a dressing having a treatment surface for applying to a treatment area of said damaged tissue;
    a pair of electrodes affixed on said treatment surface of the dressing; and
    a control unit for passing an alternating current between the electrodes to the treatment area between the electrodes and for constantly varying a value of an amplitude of the alternating current and a frequency of the alternating current to electrically stimulate and repair said damaged tissue,
    wherein the alternating current is varied between 50 and 500 microamps.

2. The device according to claim 1, wherein the control unit and the dressing are integrated with each other.

3. The device according to claim 2, wherein the control unit is etched into a substrate.

4. The device according to claim 1, wherein the frequency of the alternating current is varied between 10 and 900 hertz.

5. The device according to claim 1, wherein a time period between each variation of the amplitude is 0.1 s.

6. The device according to claim 1, wherein the alternating current has a ramp waveform.

7. The device according to claim 1, wherein the control unit comprises:
    a housing; and
    electronic circuitry in the housing connected to the pair of electrodes.

8. The device according to claim 7, wherein the electronic circuitry comprises a memory storing at least one program for determining the amplitude, the frequency and a waveform of the alternating current supplied to the electrodes.

9. The device according to claim 8, wherein the control unit further comprises an input/output port connected to the electronic circuitry, such that an external device can connect to the control unit via the input/output port and update the memory and control operation of the control unit.

10. The device according to claim 9, wherein the control unit further comprises a wireless transceiver connected to the electronic circuitry, such that the external device can wirelessly connect to the control unit via the input/output port and update the memory and control operation of the control unit.

11. The device according to claim 7, wherein the control unit comprises:
   a pair of activation electrodes; and
   a removable tab including a metallic strip connecting the activation electrodes,
   wherein the electronic circuitry detects when a current can pass between the activation electrodes and only supplies the alternating current to the pair of electrodes when the tab is removed such that no current passes between the activation electrodes.

12. The device according to claim 1, wherein the dressing is adapted to be applied to a wound.

13. The device according to claim 12, wherein the dressing is adapted to absorb an exudate from the wound.

14. The device according to claim 1, wherein the dressing comprises a tissue gel that can be absorbed by a wound.

15. The device according to claim 14, wherein the tissue gel comprises a hydropolymer that releases oxygen molecules when the alternating current flows through the tissue gel.

* * * * *